United States Patent [19]

Nelson, Jr.

[11] Patent Number: 5,854,266

[45] Date of Patent: Dec. 29, 1998

[54] SYNERGISTIC ANTIMICROBIAL COMPOSITION PYRITHIONE AND ALCOHOL

[75] Inventor: John D. Nelson, Jr., Bethlehem, Conn.

[73] Assignee: Olin Corporation, Cheshire, Conn.

[21] Appl. No.: 812,887

[22] Filed: Mar. 10, 1997

Related U.S. Application Data

[62] Division of Ser. No. 349,587, Dec. 5, 1994, Pat. No. 5,614,538.

[51] Int. Cl.$^6$ ................................................. A01K 43/40
[52] U.S. Cl. .......................... 514/345; 514/188; 514/277; 514/492; 514/730; 106/18.33
[58] Field of Search ..................... 514/345, 188, 514/277, 422, 730; 106/18.33

[56] References Cited

U.S. PATENT DOCUMENTS

| | | | |
|---|---|---|---|
| 2,809,971 | 10/1957 | Bernstein et al. | 260/270 |
| 3,159,640 | 12/1964 | McClure et al. | 260/294.8 |
| 3,236,733 | 2/1966 | Karsten et al. | 514/345 |
| 3,281,366 | 10/1966 | Judge | 514/345 |
| 4,006,218 | 2/1977 | Sipos | 424/54 |
| 4,197,318 | 4/1980 | Sipos | 424/326 |
| 4,307,089 | 12/1981 | Melloh et al. | 424/245 |

*Primary Examiner*—James H. Reamer
*Attorney, Agent, or Firm*—Dale Lynn Carlson; Todd E. Garabedian; Wiggin & Dana

[57] ABSTRACT

Disclosed herein is an antimicrobial composition characterized by synergistic antibacterial efficacy against Gram-negative bacteria and comprising an antimicrobially effective amount of a pyrithione salt or pyrithione acid, and an alcohol, preferably an aromatic alcohol. Also disclosed is a method of imparting antimicrobial activity to a composition comprising water or an organic solvent which comprises adding thereto an antimicrobially effective amount of the above-described antimicrobial composition.

12 Claims, No Drawings

SYNERGISTIC ANTIMICROBIAL COMPOSITION PYRITHIONE AND ALCOHOL

CROSS REFERENCE TO RELATED APPLICATIONS

This is a division of application Ser. No. 08/349,587, filed on Dec. 5, 1994, now U.S. Pat. No. 5,614,538 and which is incorporated herein by reference in its entirety.

FIELD OF THE INVENTION

This invention relates generally to pyrithione-containing compositions and, more specifically to such compositions having synergistic efficacy against Gram-negative bacteria.

DESCRIPTION OF THE INVENTION

Biocides provide antimicrobial protection for industrial, personal care, medical and other products and materials. Typically, a biocide will have one or more drawbacks that tends to limit its commercial usefulness, such as, for example, a somewhat limited range of antimicrobial efficacy in regard to the types of microorganisms that it will kill, or its risk of toxicity to mammals, or other adverse effect upon the environment.

The use of select classes of alcohols as so-called "potentiators" for antimicrobial agents, such as zinc pyrithione, is known, as disclosed in U.S. Pat. No. 4,006,218. The alcohols disclosed in the '218 patent are selected from the group consisting of monohydric aliphatic alcohols, cyclohexyl-substituted alkanols, phenyl alkanols of a specified structure, and phenol derivatives of a specified structure.

New combinations of pyrithione with other alcohols, exhibiting synergistic efficacy over a wide range of use concentrations, would be highly desired by the biocides community, particularly if such compositions also exhibit low toxicity against mammals. The present invention provides several of such combinations.

SUMMARY OF THE INVENTION

In one aspect, the present invention relates to an antimicrobial composition characterized by synergistic antibacterial and antifungal efficacy and comprising pyrithione acid or a pyrithione salt, or a combination thereof, and an aromatic alcohol selected from the group consisting of phenylethyl alcohol, benzyl alcohol, 2-phenoxyethanol, and combinations thereof.

In another aspect, the present invention relates to an antimicrobial composition characterized by synergistic antibacterial and antifungal efficacy and comprising pyrithione acid or a pyrithione salt, or a combination thereof, and 3-phenyl-1-propyl alcohol.

In yet another aspect, the present invention relates to a method of imparting antimicrobial activity to a composition comprising water or an aqueous organic solvent which comprises adding thereto an antimicrobially effective amount of at least one of the above-described antimicrobial compositions.

In yet another aspect, the present invention relates to a method of coating a substrate to provide an antimicrobially effective coating on the substrate which comprises contacting the substrate with a coating composition comprising at least one of the above-described antimicrobial compositions.

In still another aspect, the present invention relates to a coated substrate comprising a substrate together with a coating on said substrate, said coating being produced by (a) contacting the substrate with a coating composition comprising at least one of the above-described antimicrobial compositions, and (b) drying said coating composition on said substrate to produce said coated substrate.

In yet another aspect, the present invention relates to a paint comprising:

(a) a base medium comprising water or a resin selected from the group consisting of vinyl, alkyd, epoxy, acrylic, polyurethane and polyester resins, and combinations thereof, (b) a biocide comprising an antimicrobially effective amount of pyrithione acid or a pyrithione salt, or a combination thereof, and an alcohol, said biocide being present in an amount at least sufficient to provide inhibition of microbial growth during in-can storage of the paint. Thus, the antimicrobial composition is employed in the paint in an amount at least sufficient to act as an "in-can preservative" during storage prior to use. In addition or alternatively, the antimicrobial composition can be employed in an amount sufficient to provide antimicrobial efficacy for the paint when dried on a substrate, although suitable care should be taken to avoid leaching of the alcohol from the substrate, by using for example an encapsulant to time-regulate the release of the alcohol from the paint on the substrate.

In still another aspect, the present invention relates to a soap, shampoo or skin care medicament comprising a suitable carrier and at least one of the above-described antimicrobial compositions.

In still another aspect, the present invention relates to a metalworking fluid containing water or an organic base fluid, and at least one of the above-described antimicrobial compositions. Another aspect of the invention relates to the above-described metalworking fluid which additionally comprises a component selected from the group consisting of corrosion inhibitors, surfactants, and combinations thereof.

In yet another aspect, the present invention relates to a composition comprising a plastic or a woven or non-woven fiber which comprises, in combination, a plastic or a fiber and at least one of the above-described antimicrobial compositions.

These and other aspects will become apparent upon reading the following detailed description of the invention.

DETAILED DESCRIPTION OF THE INVENTION

It has now been surprisingly found in accordance with the present invention that the combination of pyrithione acid, or a salt thereof, with a select aromatic alcohol, as described herein, provides synergistic antimicrobial effectiveness against Gram negative bacteria.

Without wishing to be bound by any particular theory, it is believed by the present inventors that the synergistic efficacy associated with the compositions of the present invention is attributable to the mode of attack of the antimicrobial composition of the present invention in light of the unique structural configuration of Gram negative bacteria, which possess an outer cell membrane. The outer cell membrane confers resistance to certain antibiotics and biocides by preventing access to the cell membrane and interior of the cell.

Certain compounds, namely specific aromatic alcohols, have now been found by the present inventors in accordance with the present invention to act synergistically with pyrithione by facilitating the penetration of the outer cell membrane of the bacteria, thereby facilitating of the pyrithione component of the antimicrobial composition into the bacteria cell. The pyrithione then acts to collapse the proton motive force that provides the energy link for microbial metabolism, by catalyzing the electroneutral exchange of hydrogen ions and potassium ions across microbial cell membranes.

The specific aromatic alcohols employed in the present invention provide the added benefit of having a relatively low toxicity together with widespread acceptance for use as preservatives in cosmetics, pharmaceuticals, and perfumes.

The present invention permits the use of reduced amounts of the pyrithione primary biocide, in conjunction with an alcohol co-biocide that is less expensive than the primary biocide, thereby providing an antimicrobial composition that is inexpensive to produce and that possesses the above-mentioned characteristic of synergistic antimicrobial effectiveness against Gram-negative bacteria.

As use herein, the term "synergistic antimicrobial effectiveness" means that the composition exhibits greater antimicrobial activity against Gram-negative bacteria, than does the additive amounts of activity provided when each component of the combination is employed alone. The composition exhibits synergistic antimicrobial activity with respect to the growth of Gram-negative bacteria, and also provides excellent antimicrobial activity against a broad spectrum of microbes, most notably bacteria and fungi. The antimicrobial activity is provided during use of the composition, for example, in an aqueous industrial functional fluid composition, such as a metalworking fluid, lubricant, or diagnostic reagent for immunological testing, in order to provide biocidal protection against microbes such as bacteria and fungi during use of the fluid.

The pyrithione used in the process and composition of this invention is preferably a pyrithione salt, such as sodium pyrithione, zinc pyrithione, chitosan pyrithione, magnesium disulfide pyrithione, copper pyrithione, and the like, although pyrithione acid can be used if desired. More preferable pyrithione salts include sodium pyrithione, copper pyrithione, and zinc pyrithione, most preferably sodium pyrithione.

The sodium pyrithione useful in the present invention is a well-known commercial product that is commonly made by reacting 2-chloropyridine-N-oxide with NaSH and NaOH, as illustrated by the disclosures of U.S. Pat. No. 3,159,640.

Zinc pyrithione may be made by reacting 1-hydroxy-2-pyridinethione (i.e., pyrithione acid) or a soluble salt thereof with a zinc salt (e.g., $ZnSO_4$) to form a zinc pyrithione precipitate, as illustrated by the disclosures of U.S. Pat. No. 2,809,971.

In use, the antimicrobial composition of the present invention preferably contains a weight ratio of alcohol to pyrithione of between about 1:1 and about 10,000:1, more preferably between about 1:1 and about 1,250:1.

The antimicrobial compositions of the present invention are suitable for a variety of uses, such as, for example in soap, shampoo, skin care medicaments, metalworking fluids, paint, or incorporated into or onto plastic or a woven or non-woven fibers.

One significant use application for the antimicrobial compositions of the present invention is in functional fluids, such as metalworking fluids. These functional fluids are typically supplied as an aqueous concentrate containing the antimicrobial composition and the other components of the functional fluid. In the aqueous concentrate, a sufficient amount of the antimicrobial composition is provided such that the "working" functional fluid will contain a biocidally effective amount thereof. In order to satisfy this requirement, the concentrate for a metalworking fluid, for example, preferably contains a total amount of up to about 15 weight percent, or more, of the antimicrobial composition, thereby providing up to about 1,500 ppm, or more, of the antimicrobial composition in the "working" fluid based upon a dilution rate of the concentrate to the "working" fluid of between about 1:10 and about 1:100. As an illustration, a working functional fluid suitably contains about 1,000 ppm of the alcohol and about 250 ppm of the pyrithione. Other functional fluids, such as cosmetics, are often formulated directly (without the need for a concentrate) and can contain up to 5000 ppm, or more, of the antimicrobial composition.

The antimicrobial compositions of the present invention are also useful in paints, including indoor and outdoor household paints, industrial and commercial paints. Particularly advantageous results are obtained when the antimicrobial compositions of the present invention are utilized, preferably in a total amount of between about 0.01% and about 10% by weight based upon the weight of the paint, as in-can preservatives during storage and prior to use of the paint. Although, the antimicrobial compositions are also suitable for use in conjunction with marine paints for use, for example, on ship's hulls, care should be taken to avoid leaching of the alcohol component out of the paint in view of the relatively high water solubility of the alcohols. Leaching is suitably controlled by the use of known encapsulation techniques to provide a capsule comprising an alcohol core and a water-insoluble shell.

In addition, the antimicrobial compositions provide desirable results in exterior paints of the latex and alkyd types. Typically a paint composition will contain a resin, a pigment, and various optional additives such as thickening agent(s), wetting agents and the like, as is well known in the art. The resin is preferably selected from the group consisting of vinyl, alkyd, epoxy, acrylic, polyurethane and polyester resins, and combinations of thereof. The resin is preferably employed in an amount of between about 20% and about 80% based upon the weight of the paint or paint base.

In addition, the paint composition of the present invention optionally additionally contains optional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally occurring or synthetic clays, such as kaolin, montomorillonite, and bentonite), clay mica (muscovite), and chlorite (hectonite), and the like. In addition to clays other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative, thickening agents include cellulose 30 derivatives, for example methyl, hydroxyethyl, hydroxypropyl and carboxymethyl cellulose, poly(vinyl alcohol), poly(vinylpyrolidone), poly(ethyleneglycol), salts of poly(acrylic acid) and salts of acrylic acid/acrylamide copolymers.

Suitable wetting and dispersing agents include sodium polyphosphate, salts of flow molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer diols for example glycol, propylene glycol, and butylene glycol or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation (white point) of the paint composition may be reduced by adding solvents, such as ethylene glycol, butyl glycol, ethyl glycol acetate, ethyl diglycol acetate, butyl diglycol acetate, benzene or alkylated aromatic hydrocarbons. As defoaming agents there are suitable for example poly(propylene glycol) and polysiloxanes. Optionally other biocides can additionally be incorporated into the paint formulations of the present invention. Useful optional solvents include methylisobutylketone (herein referred to as "MIBK"), xylene, ethyl benzene, methanol, and combinations thereof.

The paint composition of the present invention may be used as a paint for natural or synthetic materials, for example wood, paper, metals, textiles and plastics. It is particularly suitable as an outdoor paint, and is excellent for use as a marine paint.

The compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The invention is further illustrated by the following Examples. Unless otherwise stated, the "parts" and "%" are "parts by weight" and "percent by weight", respectively.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

Mic Tests for Pyrithione Plus Alcohol

Interactions of sodium pyrithione with other compounds were assessed using a modification of the "checkerboard" MIC ("minimum inhibitory concentration") procedure described by Dougherty, et al. This procedure facilitates the measurement of the effects of a large number mixtures of different ratios of biocides. Stock solutions of pyrithiones in Tryptic Soy Broth (TSB) were diluted in TSB in microliter plates, and the test compounds were diluted in tubes of TSB. Aliquots of each dilution of test compound were added to the wells containing pyrithione dilutions and undosed TSB as a control, leaving rows of unmixed pyrithione or test compound for the determination of MIC's of pure pyrithione or test compounds. An equal volume of test culture containing $10^6$ bacteria/ml or $10^5$ fungal spores/ml suspended in TSB was added to each well, and the plates were incubated at 28° C. The lowest concentration resulting in growth inhibition (MIC) was determined. The Fractional Inhibitory Concentration (FIC), ie. ratio of the MIC of a biocide in a mixture to that of the pure substance, was determined, and the sum of the FIC's ("FIC Index") for each mixture was calculated. Each type of interaction was categorized according to the magnitude of the index: synergistic if<1; additive if=1; antagonistic if>1.

Accordingly, mixtures containing varying proportions of pyrithione and aromatic alcohols synergistically inhibited growth of a Gram-negative bacterium (i.e., *Pseudomonas aeruginosa*) and a fungus (i.e., *Aspergillus niger*), as shown by the data presented in Table 1 and Table 2, respectively, which follow.

TABLE 1

Synergistic Antibacterial Effects of Sodium Pyrithione (NPT) Mixtures MIC of Mixture (ppm)[a]

| Test Compound | Test Compound | NPT | Ratio (TC/NPT) | FIC Index[b] |
|---|---|---|---|---|
| none | 0 | 64 | — | — |
| phenoxyethanol | 5000 | 0 | — | — |
| " | 2500 | 4 | 625/1 | 0.56 |
| " | 1250 | 16 | 78/1 | 0.50 |
| " | 625 | 32 | 20/1 | 0.63 |
| " | 313 | 32 | 10/1 | 0.56 |
| " | 156 | 32 | 5/1 | 0.53 |
| benzyl alcohol | 5000 | 0 | — | — |
| " | 2500 | 8 | 313/1 | 0.63 |
| " | 1250 | 16 | 78/1 | 0.50 |
| " | 625 | 32 | 20/1 | 0.63 |
| " | 313 | 32 | 10/1 | .56 |
| phenylethyl alcohol | 5000 | 0 | — | — |
| " | 2500 | 2 | 1250/1 | 0.53 |
| " | 1250 | 16 | 78/1 | 0.50 |
| " | 625 | 32 | 20/1 | 0.63 |
| " | 313 | 32 | 10/1 | 0.56 |
| " | 156 | 32 | 5/1 | 0.53 |
| none | 0 | 128 | — | — |
| 3-phenyl-1-propyl alcohol | 2500 | 0 | — | — |
| " | 1250 | 4 | 313/1 | 0.53 |
| " | 625 | 16 | 39/1 | 0.38 |
| " | 313 | 32 | 10/1 | 0.38 |
| " | 156 | 64 | 2/1 | 0.56 |
| " | 78 | 64 | 1/1 | 0.53 |
| " | 39 | 64 | 1/2 | 0.52 |
| " | 20 | 64 | 1/3 | 0.51 |

[a]Minimum Inhibitory Concentrations (MIC's) were determined against *Pseudomonas aeruginosa* NCIMB strain 6749. NPT and inocula of bacterial cells were added to Tryptic Soy Broth (TSB) adjusted to pH 5.8. Test compounds were dissolved in TSB, and the resulting solutions were adjusted to pH 5.8 and filter-sterilized. The mixtures were diluted in TSB (pH 5.8) and incubated at 28° C. for 4 to 5 days.
[b]Fractional Inhibitory Concentration Index: additive effect if = 1; synergistic if <1; antagonistic if >1.

TABLE 2

Synergistic Antifungal Effects of Sodium Pyrithione (NPT) Mixtures
MIC of Mixture (ppm)[a]

| Test Compound | Test Compound | NPT | Ratio (TC/NPT) | FIC Index[b] |
|---|---|---|---|---|
| none | 0 | 32 | — | — |
| phenoxyethanol | 5000 | 0 | — | — |
| " | 2500 | 2 | 1250/1 | 0.63 |
| " | 1250 | 16 | 78/1 | 0.75 |
| " | 625 | 16 | 39/1 | 0.63 |
| " | 313 | 16 | 20/1 | 0.56 |
| " | 156 | 8 | 20/1 | 0.28 |
| " | 78 | 8 | 10/1 | 0.27 |
| " | 39 | 16 | 2/1 | 0.51 |
| 3-phenyl-1-propyl alcohol | 2500 | 0 | — | — |
| " | 1250 | 8 | 156/1 | 0.75 |
| " | 625 | 16 | 39/1 | 0.75 |
| " | 313 | 16 | 20/1 | 0.63 |
| " | 156 | 16 | 10/1 | 0.56 |
| " | 78 | 4 | 20/1 | 0.16 |
| " | 39 | 4 | 10/1 | 0.13 |
| none | 0 | 16 | — | — |
| phenylethyl alcohol | 5000 | 0 | — | — |
| " | 2500 | 2 | 1250/1 | 0.63 |
| " | 1250 | 8 | 156/1 | 0.75 |
| " | 625 | 16 | 39/1 | 1.13 |
| " | 313 | 4 | 78/1 | 0.31 |
| " | 156 | 8 | 20/1 | 0.53 |
| " | 78 | 4 | 20/1 | 0.27 |
| " | 39 | 8 | 5/1 | 0.51 |
| benzyl alcohol | 5000 | 0 | — | — |
| " | 2500 | 4 | 625/1 | 0.75 |
| " | 1250 | 16 | 78/1 | 1.25 |
| " | 625 | 8 | 78/1 | 0.63 |
| " | 313 | 4 | 78/1 | 0.31 |
| " | 156 | 4 | 39/1 | 0.31 |
| " | 78 | 4 | 20/1 | 0.27 |

[a]Minimum Inhibitory Concentrations (MIC's) were determined against an environmental isolate of the fungus *Aspergillus niger*. NPT and inocula of fungal spores were added to Tryptic Soy Broth (TSB) adjusted to pH 4.5. Test compounds were dissolved in TSB, and the resulting solutions were adjusted to pH 4.5 and filter-sterilized. The mixtures were diluted in TSB (pH 4.5) and incubated at 28° C. for 7 days.
[b]Fractional Inhibitory Concentration Index: additive effect if = 1; synergistic if <1; antagonistic if >1.

EXAMPLE 2

Antimicrobial Efficacy of Pyrithione and PPA Against Bacteria and Fungi

The efficacy of a sodium pyrithione +3-phenyl-1-propyl alcohol ("PPA") mixture as a preservative was measured in an oil-in-water emulsion metalworking fluid challenged with a mixture of bacteria and fungi. A 5% aqueous emulsion of concentrated MWF, consisting of mineral oil (83.5%), sulfonated hydrocarbon (10.7%), oleic acid (1.0%), triethanolamine (0.8%), methyl tallowate (3.0%), and propylene glycol ether (1.0%) was dosed with 125 ppm of sodium pyrithione and 1000 ppm of PPA and dispersed into Erlenmeyer flasks. A challenge level of $10^7$ cells of bacteria and $10^5$ fungal spores per ml of emulsion was initiated by adding a suspension of seven bacteria and two fungi originally isolated from contaminated MWF's (*Pseudomonas rubescens* NCIMB 12202, *Pseudomonas stutzeri* sp., *Pseudomonas fluorescens* NCIMB 12201, *Pseudomonas aeruginosa* NCIMB 6749, *Pseudomonas oleovorans* NCIMB 6576, *Alcaligenes faecalis* sp., *Citrobacter freundii* NCIMB 12203, *Fusarium* sp. and *Cephalosporium* sp.). The fluids were agitated continuously on a rotary shaker and sampled periodically for viable bacteria on Tryptic Soy Agar and for fungi on Tryptic Soy Agar supplemented with 100 mg gentamicin sulfate per liter. After two weeks, a pronounced inhibition of growth of bacteria and fungi was observed in the Pyrithione-PPA fluid relative to the untreated control, as shown by the results given in Table 3 below.

TABLE 3

Efficacy of Sodium Pyrithione/Phenylpropyl Alcohol Mixture in an Oil in Water Emulsion*

| | | Average Viable Count/ml | |
|---|---|---|---|
| Treatment | Time (days) | Bacteria | Fungi |
| blank | 6 | 24,200,000 | 220,000 |
| NPT (125 ppm) | 6 | 13,800,000 | 240,000 |
| PPA (1,000 ppm) | 6 | 3,670,000 | 240,000 |
| NPT (125) + PPA (1000) | 6 | 3,200,000 | 100,000 |
| blank | 13 | 21,000,000 | 240,000 |
| NPT (125 ppm) | 13 | 8,790,000 | 190,000 |
| PPA (1,000 ppm) | 13 | 2,550,000 | 130,000 |
| NPT (125) + PPA (1000) | 13 | 35,600 | 8,000 |

*5% aqueous emulsion of metalworking fluid concentrate treated with sodium pyrithione (NPT) and 3-phenyl-1-propanol (PPA).

What is claimed is:

1. A method of imparting antimicrobial activity to a composition comprising water or an aqueous organic solvent which comprises adding thereto an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol, 2-phenoxyethanol, and combinations thereof, said aromatic alcohol being present in a weight ratio between 1,250:1 and 5:1 based upon the weight of said pyrithione acid or said pyrithione salt, or combination thereof, in said antimicrobial composition.

2. The method of claim 1 wherein the weight ratio of said aromatic alcohol, to said pyrithione salt or pyrithione acid is between 78:1 and 5:1.

3. A method of coating a substrate to provide an antimicrobially effective coating on the substrate which comprises contacting the substrate with a coating composition comprising an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol. 2-phenoxyethanol, and combinations thereof, said aromatic alcohol being present in a weight ratio between 1.250:1 and 5:1 based upon the weight of said pyrithione acid or said pyrithione salt, or combination thereof, in said antimicrobial composition.

4. The method of claim 3 wherein the weight ratio of said aromatic alcohol, to said pyrithione salt or pyrithione acid is between 78:1 and 5:1.

5. A coated substrate comprising a substrate together with a coating on said substrate, said coating being produced by:
   (a) contacting the substrate with a coating composition comprising an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol. 2-phenoxyethanol, and combinations thereof, said aromatic alcohol being present in a weight ratio between 1.250:1 and 5:1 based upon the weight of said pyrithione acid or said pyrithione salt, or combination thereof, in said antimicrobial composition, to provide a coating on said substrate, and (b) drying said coating composition on said substrate to produce said coated substrate.

6. The coated substrate of claim 5 wherein the weight ratio of said alcohol, to said pyrithione salt is between 78:1 and 5:1.

7. A paint comprising:
(a) a base medium comprising water or a resin selected from the group consisting of vinyl, alkyd, epoxy, acrylic, polyurethane and polyester resins, and combinations thereof, and
(b) a biocide comprising an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol, 2-phenoxyethanol, and combinations thereof, said aromatic alcohol being present in a weight ratio between 1.250:1 and 5:1 based upon the weight of said pyrithione acid or said pyrithione salt, or combination thereof, in said antimicrobial composition, said biocide being present in an amount at least sufficient to provide inhibition of microbial growth during in-can storage of the paint.

8. The paint of claim 7 wherein said biocide is present in an amount of between about 0.01% and about 10% by weight based upon the weight of the paint.

9. A soap, shampoo or skin care medicament comprising a suitable carrier and an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol, 2-phenoxyethanol, and combinations thereof, said aromatic alcohol being present in a weight ratio between 1.250:1 and 5:1 based upon the weight of said pyrithione acid or said pyrithione salt, or combination thereof, in said antimicrobial composition.

10. A metalworking fluid containing water or an organic base fluid and an antimicrobial composition consisting essentially of at least 2 ppm of pyrithione acid or a pyrithione salt, or a combination thereof, and an aromatic alcohol selected from the group consisting of phenylethyl alcohol, benzyl alcohol, 3-phenyl-1-propyl alcohol. 2-phenoxyethanol, and combinations thereof, said aromatic alcohol being present in a weight ratio between 1,250:1 and 5:1 based upon the weight of said pyrithione acid or said pyrithione salt, or combination thereof, in said antimicrobial composition.

11. The metalworking fluid of claim 10 which additionally contains a component selected from the group consisting of corrosion inhibitors, surfactants, and combinations thereof.

12. A composition comprising a plastic or a woven or non-woven fiber which comprises, in combination, a plastic or a fiber and an antimicrobial composition consisting essentially of at least 2 ppm of pyrithione acid or a pyrithione salt, or a combination thereof, and an aromatic alcohol selected from the group consisting of phenylethyl alcohol, benzyl alcohol. 3-phenyl-1-propyl alcohol, 2-phenoxyethanol, and combinations thereof, said aromatic alcohol being present in a weight ratio between 1.250:1 and 5:1 based upon the weight of said pyrithione acid or said pyrithione salt, or combination thereof, in said antimicrobial composition.

* * * * *